United States Patent [19]

Slone

[11] Patent Number: 5,318,446
[45] Date of Patent: Jun. 7, 1994

[54] TOOL AND METHOD FOR ACHIEVING CONSISTENT INTERPROXIMAL DENTAL CONTACTS

[76] Inventor: Charles E. Slone, 27552 Escuna, Mission Viejo, Calif. 92692

[21] Appl. No.: 935,708

[22] Filed: Aug. 25, 1992

[51] Int. Cl.$^5$ .......................... A61C 7/00; A61C 5/04
[52] U.S. Cl. ........................................................ 433/149
[58] Field of Search ............... 433/141, 148, 149, 155, 433/162, 226, 215, 39, 143, 144

[56] References Cited

U.S. PATENT DOCUMENTS

| | | | |
|---|---|---|---|
| 1,109,924 | 9/1914 | Hoffman et al. | 433/144 |
| 1,691,786 | 11/1928 | Roth | 433/143 |
| 2,138,726 | 11/1938 | Cartwright | 433/144 X |
| 2,439,703 | 4/1948 | Tofflemire | 433/155 |
| 2,602,998 | 7/1952 | Sprague | 433/141 |
| 4,365,957 | 12/1982 | Das | 433/144 |
| 4,578,035 | 3/1986 | Pruitt | 433/149 |
| 4,608,021 | 8/1986 | Barrett | 433/229 |
| 4,726,770 | 2/1988 | Kurer | 433/229 |
| 4,836,781 | 6/1989 | Meinershagen | 433/141 |

Primary Examiner—Gene Mancene
Assistant Examiner—Nickolas D. Lucchesi
Attorney, Agent, or Firm—Gene Scott

[57] ABSTRACT

An apparatus and method is provided for preparing a tight proximal contact between a tooth to be filled and an adjacent tooth. A tool head provides a first convex surface extending downwardly to a linear ridge. The head is divided into a pair of side-by-side fingers separated by a channel. The linear ridge defines the tip of each finger. The head is of a size to fit into a prepared cavity in a tooth. The head further provides a stepped surface, in opposition to the first convex surface, that extends downwardly to the linear ridge. Alternately, the head provides a second convex surface, in opposition to the first convex surface, that extends downwardly to the linear ridge. An elongated tool handle has a first and a second opposing bent ends. The first bent end has a 90° bend, and the second bent end has a 45° bend, such that the single tool may enable the formation of both distal and mesial contacts.

10 Claims, 2 Drawing Sheets

TOOL AND METHOD FOR ACHIEVING CONSISTENT INTERPROXIMAL DENTAL CONTACTS

FIELD OF THE INVENTION

This invention relates generally to dental tools for tooth restoration, and, more particularly, is directed towards a dental tool for achieving proper tooth positioning between a tooth to be filled and an adjacent tooth.

BACKGROUND OF THE INVENTION

Normally, adjacent healthy teeth are in proximal contact with each other at a proximal contact point. However, if a tooth experiences decay or otherwise experiences damage, its contact point with the adjacent tooth may be lost. During restoration of the tooth, therefore, it is important for the dental practitioner to restore a proper contact point with the adjacent tooth. The recent increase in popularity of resin-based light-curable filling materials has resulted in new procedures, and new difficulties, in establishing proximal contact between adjacent teeth, and tooth restoration in general.

Several prior art devices and methods have been developed for facilitating the establishment of a proximal contact point between adjacent teeth. For example, U.S. Pat. No. 4,608,021, issued to Barrett on Aug. 26, 1986, teaches a device and method for proper relative positioning of adjacent teeth during a restoration procedure. A small rigid wedge with a shorter side and a longer side is first inserted with the shorter side against a prepared pulpal floor. A ledge of cured restorative material is formed about the pointed end of the wedge. Thereafter, the wedge is removed and reinserted with the longer side toward the pulpal floor. The longer side is sized such that a downward force on the wedge deforms a matrix band and causes proper spacing between the two adjacent teeth. Use of such a device, however, has significant drawbacks. First, the amount of separation between the teeth is dependent upon the size and shape of the wedge. As such, the dental practitioner must properly estimate which wedge size and shape to use prior to the step of building up a pivoting ledge on the pulpal floor. Such an estimation is difficult at best, especially when considering the necessarily small sizes of such wedges. Moreover, once restorative material has been built-up around this type of wedge, the wedge must be removed in order to complete the restoration process. However, removal of the wedge necessarily removes the artificial contact point that had been established between the wedge and the adjacent tooth. As such, the adjacent tooth tends to deform the matrix band back toward the tooth being restored, causing successive layers of restorative material to also assume a slightly less than optimal shape. As a result, not only is this type of device difficult to work with, but use of this type of device and method does not result in an optimal contact point between adjacent teeth.

Another prior art device and method for use are taught in U.S. Pat. No. 4,726,770, issued to Kurer on Feb. 23, 1988. A performed body is positioned in a tooth cavity and held in pressure contact with a matrix band against an adjacent tooth. The cavity is then filled with restorative material, which is then cured by light. Such a pre-formed body, however, must remain in the cavity as the tooth is completely restored. As such, a properly sized preformed body must be selected by the dental practitioner before completely restoring the tooth. Making such a selection properly can be difficult, especially when taking into consideration the necessarily small sizes of such pre-formed bodies. Moreover, such a preformed body must be shaped to engage a hand instrument that is used to apply pressure to the preformed body. However, such an engagement means experiences a high degree of force due to the leverage excerpted by the hand instrument against the adjacent tooth. Such engagement means, therefore, are inclined to break if excessive force is applied thereto. Such breakage frequently occurs well before sufficient force as been applied to the tooth and the adjacent tooth. Moreover, when such breakage occurs, considerable injury may result to the patient's month due to the hand instrument suddenly being released from the performed body. Further, the restoration resulting from use of such a device is heterogeneous, and is therefore more difficult to shape and polish in a consistent fashion. For example, while the restorative material may be shaped easily, the preformed body may not lend itself to shaping as easily. As such, devices and methods of this type are difficult to use.

Clearly, then, there is a need for a dental implement and method that will facilitate the establishment of tight proximal contacts between a tooth and an adjacent tooth easily, quickly, and safely. Such a needed device would facilitate the establishment of both distal and mesial contacts, and would not require the dental practitioner to select a small, correctly sized wedge or preformed body. Use of such a needed device would create a proper proximal contact point and maintain the same throughout the procedure. The resulting restoration would be of a homogeneous mixture of filler material, making the final shaping and polishing of the restoration easy and consistent. Moreover, such a needed device would be extremely easy to manufacture, use, and clean. The present invention fulfills these needs and provides further related advantages.

SUMMARY OF THE INVENTION

The present invention is a tool for preparing a tight proximal contact between a tooth to be filled and an adjacent tooth. A tool head provides a first convex surface extending downwardly to a linear ridge. The head is divided into a pair of side-by-side fingers separated by a channel. The linear ridge defines the tip of each finger. The head is of a size to fit into a prepared cavity in a tooth. An elongated tool handle has a first end defined by a first bend in the handle. The first end fixedly supports the head. The channel is aligned with a longitudinal axis of the handle so that with the handle held in a near horizontal orientation, the head is positionable inside the cavity with the tips of the fingers in contact with a floor of the cavity. As such, the orientation of the handle clearly indicates the orientation of the head, even when the head is difficult to see while in use. The head further provides a stepped surface, in opposition to the first convex surface, that extends downwardly to the linear ridge. Alternately, the head provides a second convex surface, in opposition to the first convex surface, that extends downwardly to the linear ridge. A guide indicia may be included on the head to indicate proper alignment with the adjacent tooth, and to indicate proper proximal floor depth in the tooth to be filled.

The second end of the handle is defined by a second bend in the handle and further includes a second tool head. The second tool head is essentially identical to the first tool head, but is fixedly supported to the second end. The channel of the second tool head has a common orientation with the channel of the first tool head. The convex surface of each of the tool heads face in the same general direction. The first bend is preferably a 90° bend to facilitate the formation of distal contacts. Alternately, the first bend may be a 45° bend to facilitate the formation of mesial contacts. In the preferred embodiment of the invention, the first bend is a 90° bend, and the second bend is a 45° bend, such that the single tool may enable the formation of both distal and mesial contacts. Preferably, the entire tool, or at least the head of the tool, is manufactured from a transparent material, such as a hard transparent plastic, in order to allow the passage of light to enable light curing of a filler material.

The present invention facilitates the establishment of tight proximal contacts between a tooth and an adjacent tooth easily, quickly, and safely. The present invention works equally well for both distal and mesial contacts, and does not require the dental practitioner to select a small, correctly sized wedge or preformed body. Use of the present device creates a proper proximal contact point and maintains the same throughout the procedure. Moreover, the resulting restoration is of a homogeneous mixture of filler material, making the final shaping and polishing of the restoration easy and consistent. Further, the present device is extremely easy to manufacture, use, and sterilize. Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
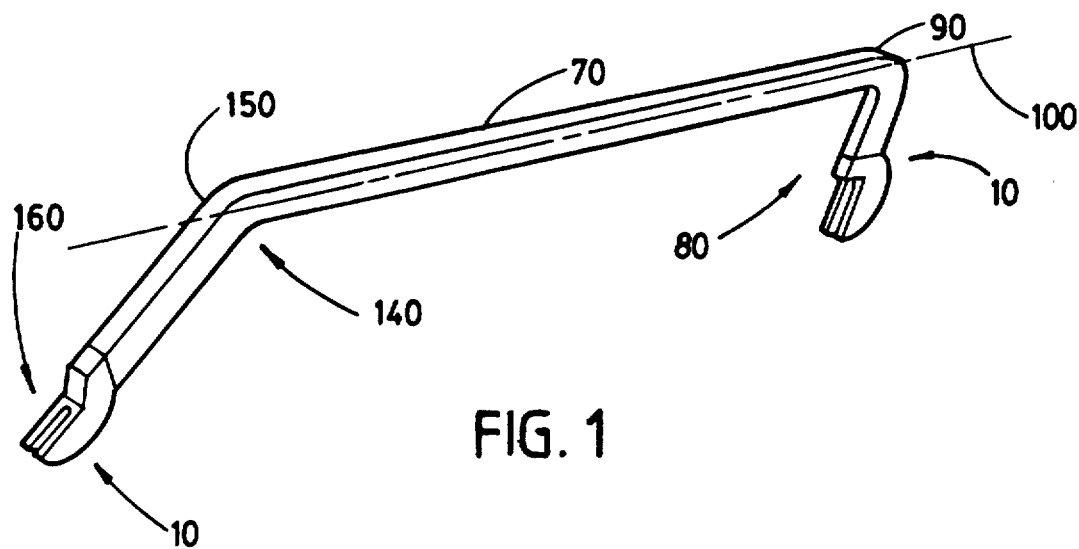
FIG. 1 is a side elevation view of the invention, illustrating a handle with a first tool head on a first bent end, and a second tool head on a second bent end.
Figure 2:
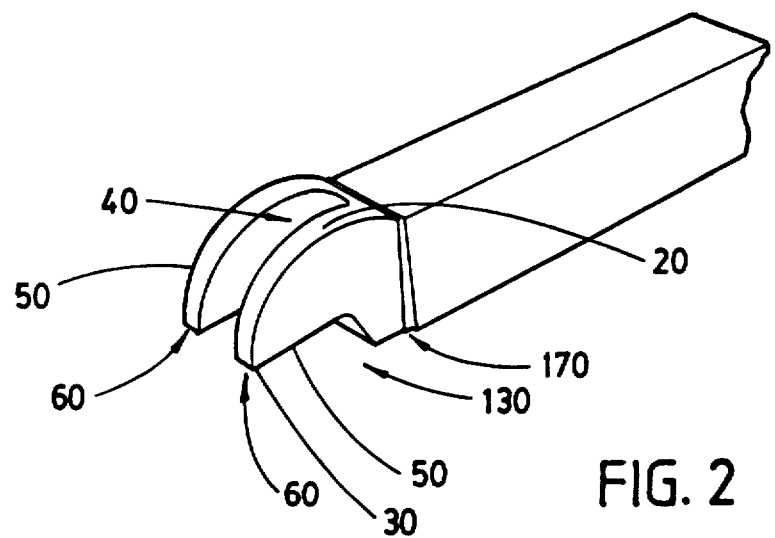
FIG. 2 is a perspective illustration of the first tool head of FIG. 1, illustrating a first convex surface and a stepped surface of a pair of fingers.

FIGS. 1 and 2 show a tool for preparing a tight proximal contact between a tooth 5 to be filled and a neighboring tooth 6. A tool head 10 provides a first convex surface 20 extending downwardly to a linear ridge 30. The head 10 is divided into a pair of side-by-side fingers 50 separated by a channel 40. The linear ridge 30 defines the tip 60 of each finger 50. The head 10 is of a size to fit into a prepared cavity 7 in the tooth 5.

An elongated tool handle 70 has a first end 80 defined by a first bend 90 in the handle 70. The first end 80 fixedly supports the head 10. The channel 40 is aligned with a longitudinal axis 100 of the handle 70 so that with the handle 70 held in a near horizontal orientation, the head 10 is positionable inside the cavity 7 with the tips 60 of the fingers 50 in contact with a floor 8 of the cavity 7. As such, the orientation of the handle 70 clearly indicates the orientation of the head 10, even when the head 10 is difficult to see while in use.

Figure 3:
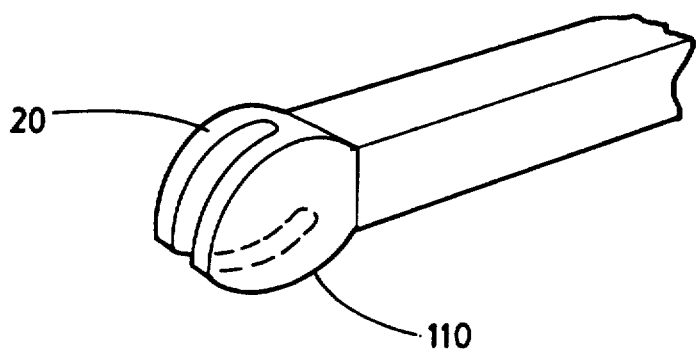
FIG. 3 is a perspective illustration of an alternate embodiment of the first tool head of FIG. 1, illustrating the first convex surface and a second convex surface.

In one embodiment of the invention, the head 10 further provides a stepped surface 130 in opposition to the first convex surface 20, that extends downwardly to the linear ridge (FIG. 2). A guide indicia 170 may be included on the head 10 to indicate proper alignment with the adjacent tooth 6, and to indicate proper proximal floor depth in the tooth 5 to be filled. In an alternate embodiment of the invention, the head 10 instead provides a second convex surface 110, in opposition to the first convex surface 20, that extends downwardly to the linear ridge 30 (FIG. 3).

The second end 140 of the handle 70 may be defined by a second bend 150 in the handle 70 and may further include a second tool head 160. The second tool head 160 is essentially identical to the first tool head 10, but is fixedly supported to the second end 140. The channel 40 of the second tool head 160 has a common orientation with the channel 40 of the first tool head 10. The convex surface 20 of each of the tool heads 10,160 face in the same general direction. The first bend 90 is preferably a 90° bend to facilitate the formation of distal contacts. Alternately, the first bend 90 may be a 45° bend to facilitate the formation of mesial contacts. In the preferred embodiment of the invention, the first bend 90 is a 90° bend, and the second bend 150 is a 45° bend, such that the single tool may enable the formation of both distal and mesial contacts. Preferably, the entire tool, or at least the head 10 of the tool, is manufactured from a transparent material, such as a hard transparent plastic, in order to allow the passage of light to enable light curing of a filler material 200.

Figure 4:
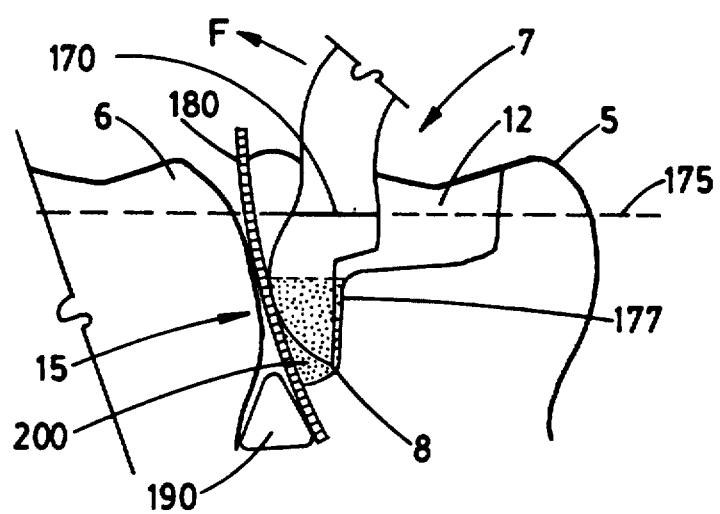
FIG. 4 is a cross-sectional view of a tooth to be filled and an adjacent tooth, illustrating the initial positioning of the tool head of FIG. 2 in a prepared cavity, and, in phantom outline, the desired positioning of the teeth by levering of the tool head.

In operation, a proximal box 12 with a pulpal floor 8 in a tooth 5 to be filled is prepared in a conventional manner (FIG. 4). If extensive tooth decay necessitates a deeper pulpal floor 8, then the pulpal floor 8 may be built-up with filler material 200 such that the convex surface 20 of the head 10, when the head 10 is inserted into the prepared cavity 7, will contact the junction 15 of the incisal and middle third of the tooth 5 for filling. Alternatively, the indicia 170 may be aligned with the marginal ridge 175 of the companion tooth 6 to indicate proper pulpal floor depth. If necessary, the pulpal floor level may be built-up with filler material 200 and hardened so that a step 177 may be prepared in the pulpal floor 8 to form an axial wall. The step 177 is for accepting the stepped surface 130 and the fingers 50 of the head 10.

A matrix band 180 is then placed between the tooth 5 to be filled and a companion tooth 6 adjacent to the proximal box 12. A wedge 190, such as a conventional wooden wedge, is placed under the matrix band 180 to support the matrix band 180 against the tooth 5 to be filled. Then approximately one-half of the volume of the proximal box 12 is filled with a hardenable filler material 200. The head 10 of the tool is placed into the proximal box 12 such that the fingers 50 are immersed in the filler material 200. The fingers 50 engage the axial wall so that the convex surface 20 is in contact with the companion tooth 6 through the matrix band 180. The head 10 is rotated by applying force F to the handle 70 (FIG. 4) such that the head is rotated, forcing the convex surface 20 against the companion tooth 6. The tips 60 of the fingers 50 are pressed against the step 177 at the pulpal floor 8, acting as a fulcrum and forcing the convex surface 20 against the companion tooth 6, such that a desired spacing is achieved between the tooth 5 to be filled and the companion tooth 6. The desired spacing is held by maintaining the level of the handle 70 while the filler material 200 is hardened in order to produce a bridge structure 210 (FIG. 6) of the hardened filler material 200 in the channel 40 between the fingers 50. The hardened bridge structure 210 extends between the step 177 in the pulpal floor 8 and the matrix band 180. Upon removing the tool, the bridge structure 210 is left to maintain the desired spacing between the tooth 5 to be filled and the companion tooth 6. The remainder of the volume of the proximal box 12 is filled, including the channels formed by the head 10, with the filler material 200. The remaining filler material 200 is then hardened and finished in the conventional manner until the tooth 5 to be filled has been restored.

Figure 5:
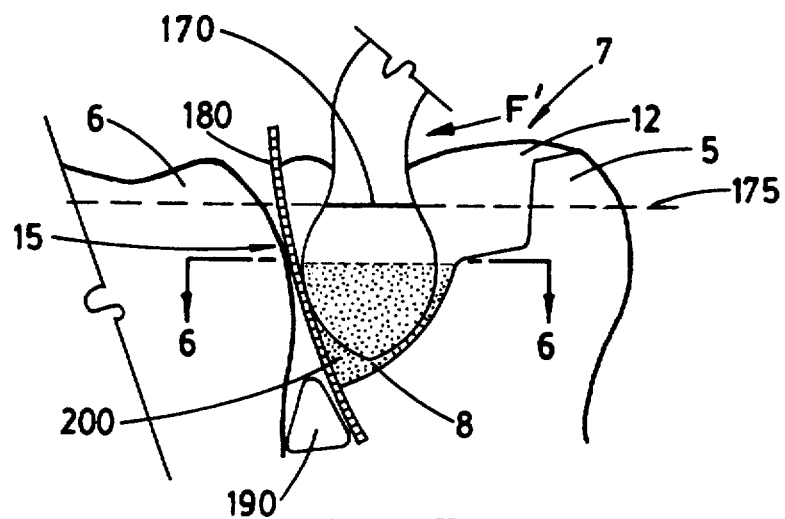
FIG. 5 is a cross-sectional view of the tooth to be filled and an adjacent tooth, illustrating the initial positioning of the tool head of FIG. 3 in a prepared cavity without a prepared step.

In the embodiment wherein the second convex surface 110 is provided on the head 10, one of the convex surfaces 20,110 is forced against the companion tooth 6 by manual pressure F' (FIG. 5), and not by changing the elevation of the handle 70, in order to achieve the desired spacing between the tooth 5 to be filled and the companion tooth 6. In such an embodiment, a step 177 does not have to be formed in the pulpal floor 8 before filling the proximal box 12 with the filling material 200.

Figure 6:
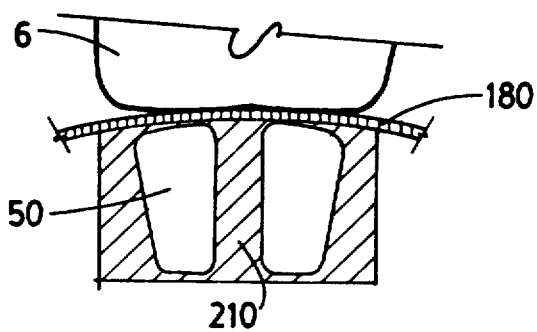
FIG. 6 is a cross-sectional view of the fingers of the head of the present invention, taken generally along lines 6—6 of FIG. 4, illustrating a preferred convex surface of the fingers and the resulting shape of a bridge structure formed between the teeth.

Preferably, the fingers 50 are convex in shape along the length of the first convex surface 20 so that the bridge structure 210 formed between the fingers 50 is wider at the matrix band 180 and at the step 177 (FIG. 6). Such convex shaped fingers 50 are also easier to remove from the hardened filler material 200. Clearly, head 10 and fingers 50 may be made of various sizes that are appropriate for various sizes of teeth and individuals.

Clearly, in operation, the head 10 could be inserted into the proximal box 12 before filling the proximal box 12 with any filler material 200. However, it has been found that by filling the proximal box 12 with filler material 200 first, and then inserting the head 10, the filler material 200 is more evenly distributed within the proximal box 12 and better conforms thereto. Before inserting the head 10, filler material 200 can also be inserted into the channel 40 of the head 10.

While the invention has been described with reference to a preferred embodiment, it is to be clearly understood by those skilled in the art that the invention is not limited thereto. Rather, the scope of the invention is to be interpreted only in conjunction with the appended claims.

What is claimed is:

1. A tool for preparing tight interproximal contacts between teeth comprising:

a tool head providing a first convex surface extending downwardly to a linear ridge, the head being divided into a pair of side-by-side fingers separated by a channel, the linear ridge defining the tips of the fingers, the head being of a size to fit into a prepared cavity in a tooth;

an elongated tool handle having a first bend therein and having a first end fixed rigidly to the head in support thereof, so that when the head is positioned inside the cavity and, the tips of the fingers are in contact with a floor of the cavity, the handle extends outwardly from the tooth, in position for manual manipulation of the handle;

the tool head being of a material of construction that is transparent to the passage of light to enable light curing of a filler material.

2. The tool of claim 1 wherein the head further provides a second convex surface in opposition to the first convex surface, the second convex surface extending downwardly to the linear ridge.

3. The tool of claim 1 wherein the head further provides a stepped surface in opposition to the first convex surface, the stepped surface extending downwardly to the linear ridge.

4. The tool of claim 1 wherein the first bend is a 90 degree bend to enable distal contacts.

5. The tool of claim 1 wherein the first bend is a 45 degree bend to enable mesial contacts.

6. The tool of claim 1 wherein the handle has a second end defined by a second bend in the handle and further including a second tool head essentially identical to the first tool head, fixed to the second end in support thereof, the channel of the second tool head having a common orientation with the channel of the first tool head, the convex surface of each of the tool heads facing in the same general direction.

7. A method for achieving consistent interproximal dental contacts comprising the steps:

a) providing a tool with a handle supporting a head comprising a pair of parallel downwardly extending fingers, defining a channel one side of the fingers defining a convex surface, the surface meeting at a linear ridge defining the tips of the fingers;

b) preparing a proximal box with a pulpal floor in a tooth to be filled such that the pulpal floor contains a step for accepting the fingers;

c) placing a matrix band between the tooth to be filled and a companion tooth adjacent to the proximal box;

d) placing a wedge under the matrix band in support thereof;

e) preparing the proximal box for filling;

f) filling approximately one-half of the volume of the proximal box with a hardenable filler material;

g) placing the head of the tool into the proximal box such that the fingers are immersed in the filler material, the fingers engaging the axial wall so that the convex surface is in contact with the companion tooth through the matrix band;

h) rotating the head to force the convex surface against the companion tooth by changing the elevation of the handle, the tips of the fingers pressing against the step in the pulpal floor forcing the convex surface against the companion tooth, such that a desired spacing is achieved between the tooth to be filled and the companion tooth;

i) holding the desired spacing by maintaining the level of the handle, while the filler material is hardened in order to produce a bridge structure in the channel between the fingers of the hardened filler material, said bridge structure extending between the step in the pulpal floor and the matrix band;

j) removing the tool, leaving the bridge structure to maintain the desired spacing between the tooth to be filled and the companion tooth;

k) filling the remainder of the volume of the proximal box, with the filler material;

l) hardening and finishing the filler material until the tooth to be filled is restored.

8. The method of claim 7 further including the step, performed after step (b), of building the pulpal floor to a level such that the convex surface is most likely to contact the junction of the incisal and middle third of the tooth for filling.

9. The method of claim 7 further including the step, performed after step (b), of building the pulpal floor level so that a step may be prepared in the pulpal floor.

10. A method for achieving consistent interproximal dental contacts comprising the steps:

a) providing a tool with a handle supporting a head comprising a pair of parallel downwardly extending fingers, opposite sides of the fingers defining convex surfaces, the surfaces meeting at a linear ridge defining the tips of the fingers;

b) preparing a proximal box with a pulpal floor in a tooth to be filled such that the pulpal floor contains a step for accepting the fingers;

c) placing a matrix band between the tooth to be filled and a companion tooth adjacent to the proximal box;

d) placing a wedge under the matrix band in support thereof;

e) preparing the proximal box for filling;

f) filling approximately one-half of the volume of the proximal box with a hardenable filler material;

g) placing the head of the tool into the proximal box such that the fingers are immersed in the filler material, the fingers engaging the axial wall so that one of the convex surfaces is in contact with the companion tooth through the matrix band;

h) forcing one of the convex surfaces against the companion tooth by manual pressure such that a desired spacing is achieved between the tooth to be filled and the companion tooth;

i) holding the desired spacing by maintaining the level of the handle, while the filler material is hardened in order to produce a bridge structure of the hardened filler material, said bridge structure formed between the downwardly extending fingers and extending between the step in the pulpal floor and the matrix band;

j) removing the tool, leaving the bridge structure to maintain the desired spacing between the tooth to be filled and the companion tooth;

k) filling the remainder of the volume of the proximal box, with the filler material;

l) hardening and finishing the filler material until the tooth to be filled is restored.

* * * * *